(12) United States Patent
Nakamori et al.

(10) Patent No.: US 7,314,745 B2
(45) Date of Patent: Jan. 1, 2008

(54) PROTEIN AND DNA ENCODING THE SAME

(75) Inventors: Shigeru Nakamori, Fukui-Ken (JP); Hiroshi Takagi, Fukui (JP); Masakazu Takahashi, Fukui (JP); Kazuhisa Tsujimoto, Fukui (JP); Hideyuki Yamada, Fukui (JP)

(73) Assignee: Seiren Kabushiki Kaisha, Fukuii-Ken (JP)

( * ) Notice: Subject to any disclaimer, the term of this patent is extended or adjusted under 35 U.S.C. 154(b) by 708 days.

(21) Appl. No.: 10/469,486

(22) PCT Filed: Mar. 1, 2002

(86) PCT No.: PCT/JP02/01934

§ 371 (c)(1),
(2), (4) Date: Aug. 29, 2003

(87) PCT Pub. No.: WO02/070688

PCT Pub. Date: Sep. 12, 2002

(65) Prior Publication Data

US 2004/0096862 A1    May 20, 2004

(30) Foreign Application Priority Data

Mar. 2, 2001   (JP) ............................. 2001-059057

(51) Int. Cl.
*C12N 9/64*     (2006.01)
*C12N 15/57*    (2006.01)
*C12N 15/79*    (2006.01)
*C12N 15/85*    (2006.01)

(52) U.S. Cl. .................. 435/226; 435/69.1; 435/252.3; 435/320.1; 536/23.2

(58) Field of Classification Search .................... None
See application file for complete search history.

(56) References Cited

U.S. PATENT DOCUMENTS 5,399,283 A * 3/1995 Stabinsky et al. .......... 510/392
6,406,900 B1 * 6/2002 Hunter et al. ............... 435/212

OTHER PUBLICATIONS

Mazumdar-Geighton, S. et al., Identification of novel serine proteinase gene transcripts in the midgets of two tropical insect pest, *Scirpophaga incertulas* (Wk.) and *Helicoverpa armigera* (Hb.), Insect Biochemistry and Molecular Biology, 2000, vol. 30, No. 1, pp. 57 to 68.

(Continued)

*Primary Examiner*—Kathleen Kerr Bragdon
*Assistant Examiner*—William W. Moore
(74) *Attorney, Agent, or Firm*—Ladas and Parry LLP

(57) ABSTRACT

An objective of the present invention is to provide a new protein derived from the silkworm middle silk gland and a DNA encoding said protein. The present invention relates to a protein of the following (a) or (b): (a) a protein comprising the amino acid sequence represented by SEQ ID NO: 1; (b) a protein comprising a modified amino acid sequence of the amino acid sequence described in (a) above, in which one or more amino acid residues are deleted, substituted, inserted or added, and having protease activity.

9 Claims, 8 Drawing Sheets

CONSERVED SEQUENCE OF    VLS<u>AAHC</u> <------ ABOUT 450 bases ------> C<u>QGDSGGP</u>---
SERINE PROTEASE PRIMER SET-UP POSITION    →
                        primer1                              ← primer2
                                                             ←
                                                             primer3

OTHER PUBLICATIONS

Lehane, S.M. et al., Cloning, sequencing, temporal expression and tissue-specificity of two serine proteases from the midgut of the blood-feeding fly *Stomoxys calcitrans*., Eur.J.Biochem., 1998, vol. 254, No. 2, pp. 290 to 296.

Kotani, E. et al., Cloning and sequence of a cDNA for a highly basic protease from the digestive juice of the silkworm, Bombyx mori., Insect Mol Biol, 1999, vol. 8, No. 2, pp. 299 to 304.

Jiang, H. et al., Four serine proteinases expressed in Manduca sexta haemocytes, Insect Mol Biol, 1999, vol. 8, No. 1, pp. 39 to 53.

Adams, M.D., et al. "The Genome Sequence of *Drosophila melanogaster*" American Association for the Advancement of Science (2000) vol. 287, pp. 2185-2195 XP-000961051.

Database Uniprot. Adams, M.D., et al. "The genome sequence of *Drosophila melanogaster*" EBI (2000) XP-002288320.

\* cited by examiner

CONSERVED SEQUENCE OF  VLSAAHC <------ ABOUT 450 bases ------> CQGDSGGP---
SERINE PROTEASE PRIMER SET-UP POSITION  ⟶                              ⟵
                                    primer1                      primer2
                                                                                      ⟵
                                                                                                primer3

F I G. 1

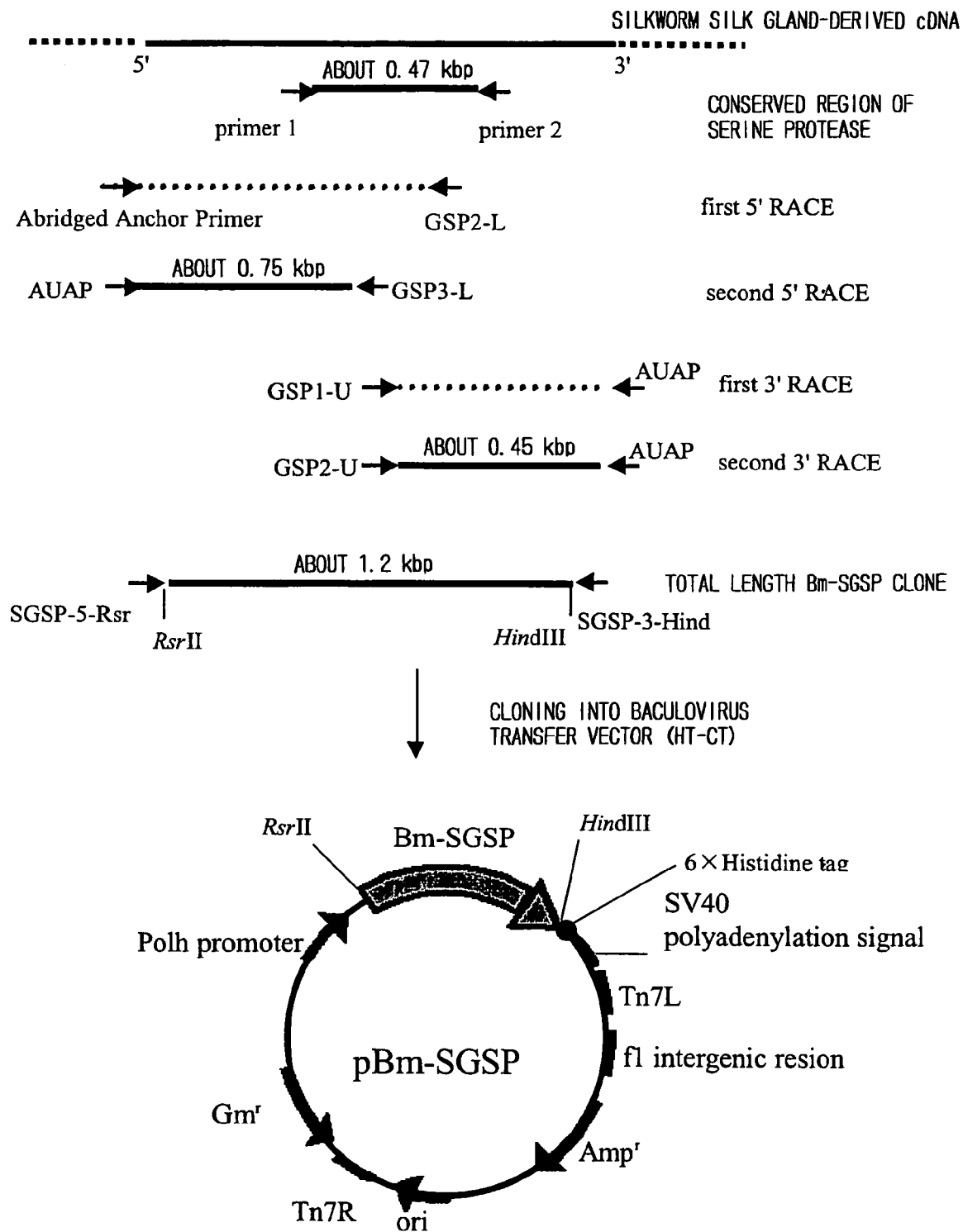
F I G. 2

```
  1 ATGTGCCTTGAACTTGTATTGGTTGTACTGGCCTTGAATGGCGTGTTATCACAGAGCCCG       60

1 MetCysLeuGluLeuValLeuValValLeuAlaLeuAsnGlyValLeuSerGlnSerPro       20

61 GGATGCGACTTTGCGCAAAATATTGCCGTCGGAACTACGGTGGATATAAGCAGTCCGGGT      120

21 GlyCysAspPheAlaGlnAsnIleAlaValGlyThrThrValAspIleSerSerProGly       40

121 TACCCCGGCAACTACCGTCCCGGTATTCAATGTAGATGGATAGCGACATGTCCCGTTGGA      180

41 TyrProGlyAsnTyrArgProGlyIleGlnCysArgTrpIleAlaThrCysProValGly       60

181 TACAATTGTCAAATAGATTGCCCCATAATCTCCATACCCCAAAGTTCTTCTTGCATAGAT      240

61 TyrAsnCysGlnIleAspCysProIleIleSerIleProGlnSerSerSerCysIleAsp       80

241 CGACTATTGCTCTCAAGGACGGGTGACCCCCAATTGAGTGGAGCCGAAGTCTACTGCGGG      300

81 ArgLeuLeuLeuSerArgThrGlyAspProGlnLeuSerGlyAlaGluValTyrCysGly      100

301 AGAGGAACTTTATCTGCAACTTCTGTTGGCCAGAGACTTAGTTTGGGGTTGATATCTTCA      360

101 ArgGlyThrLeuSerAlaThrSerValGlyGlnArgLeuSerLeuGlyLeuIleSerSer      120

361 AACTCAAGTCCCGGTGGATACTTCAGGTGTCGCGTATACGCGGTGGCATCAGCTCCTAGT      420

121 AsnSerSerProGlyGlyTyrPheArgCysArgValTyrAlaValAlaSerAlaProSer      140

421 CCAGCACCTTGCAGATGCGGGGAAAGGAAACAGACCCGCATTGTGGGGGGTGAAGAGGCG      480

141 ProAlaProCysArgCysGlyGluArgLysGlnThrArgIleValGlyGlyGluGluAla      160

481 AAAATCAATGAATTCCGAATGATGGTCGGGTTAGTTGATATCAGCATCAGGCAAATCAAA      540

161 LysIleAsnGluPheArgMetMetValGlyLeuValAspIleSerIleArgGlnIleLys      180

541 TGCGGAGGCGCCTTGATCTCTAATAGACATGTACTGACCGCAGCCCATTGTATTGCCAAC      600

181 CysGlyGlyAlaLeuIleSerAsnArgHisValLeuThrAlaAlaHisCysIleAlaAsn      200
```

FIG. 3a

```
601 CAAAGAACGGATAACATAGGAGTTATAGTTGGAGAACACGATGTTTCCAGCGGCACAGAA        660
201 GlnArgThrAspAsnIleGlyValIleValGlyGluHisAspValSerSerGlyThrGlu        220

661 TCGGCAGCTCAGGGTTACGTAGTACAAAGGTTTATTATACATCCATTATTTACTGCTTCC        720
221 SerAlaAlaGlnGlyTyrValValGlnArgPheIleIleHisProLeuPheThrAlaSer        240

721 AATTATGACTACGACGTGGCGATAGTGGAAACAACAAAGGAAATAACATTCAGCGATATA        780
241 AsnTyrAspTyrAspValAlaIleValGluThrThrLysGluIleThrPheSerAspIle        260

781 GTTGGACCGGCTTGTCTACCGTTCAAGTTCGTCAATACCAATTTCACTGGCTTAAAAGTT        840
261 ValGlyProAlaCysLeuProPheLysPheValAsnThrAsnPheThrGlyLeuLysVal        280

841 ACCATTCTTGGTTGGGGAACGTTATTCCCGGGAGGTCCAACGTCTAATGTTCTCCGTAAG        900
281 ThrIleLeuGlyTrpGlyThrLeuPheProGlyGlyProThrSerAsnValLeuArgLys        300

901 GTAGACCTGGACGTCATCAGCCAGAGCACCTGTAGGAGTTACGAGTCGACACTGACGGAC        960
301 ValAspLeuAspValIleSerGlnSerThrCysArgSerTyrGluSerThrLeuThrAsp        320

961 AGACAGATGTGCACATTCACTCCTGGGAAGGACGCGTGTCAAGACGACTCCGGTGGCCCT       1020
321 ArgGlnMetCysThrPheThrProGlyLysAspAlaCysGlnAspAspSerGlyGlyPro        340

1021 CTGCTCTATACAGACCCGAGTACCGGATTGTTCTTCAACCTGGGCATCGTGAGTTACGGT       1080
341  LeuLeuTyrThrAspProSerThrGlyLeuPhePheAsnLeuGlyIleValSerTyrGly        360

1081 CGTTTCTGCGCATCAAACAGTCCGGGCATCAACATGAGAGTCACCGCAGTACTGGACTGG       1140
361  ArgPheCysAlaSerAsnSerProGlyIleAsnMetArgValThrAlaValLeuAspTrp        380

1141 ATCGTCTCGTCCACGCAATATAACTTCTGCAGGAAATAA                            1179
381  IleValSerSerThrGlnTyrAsnPheCysArgLys***                            392
```

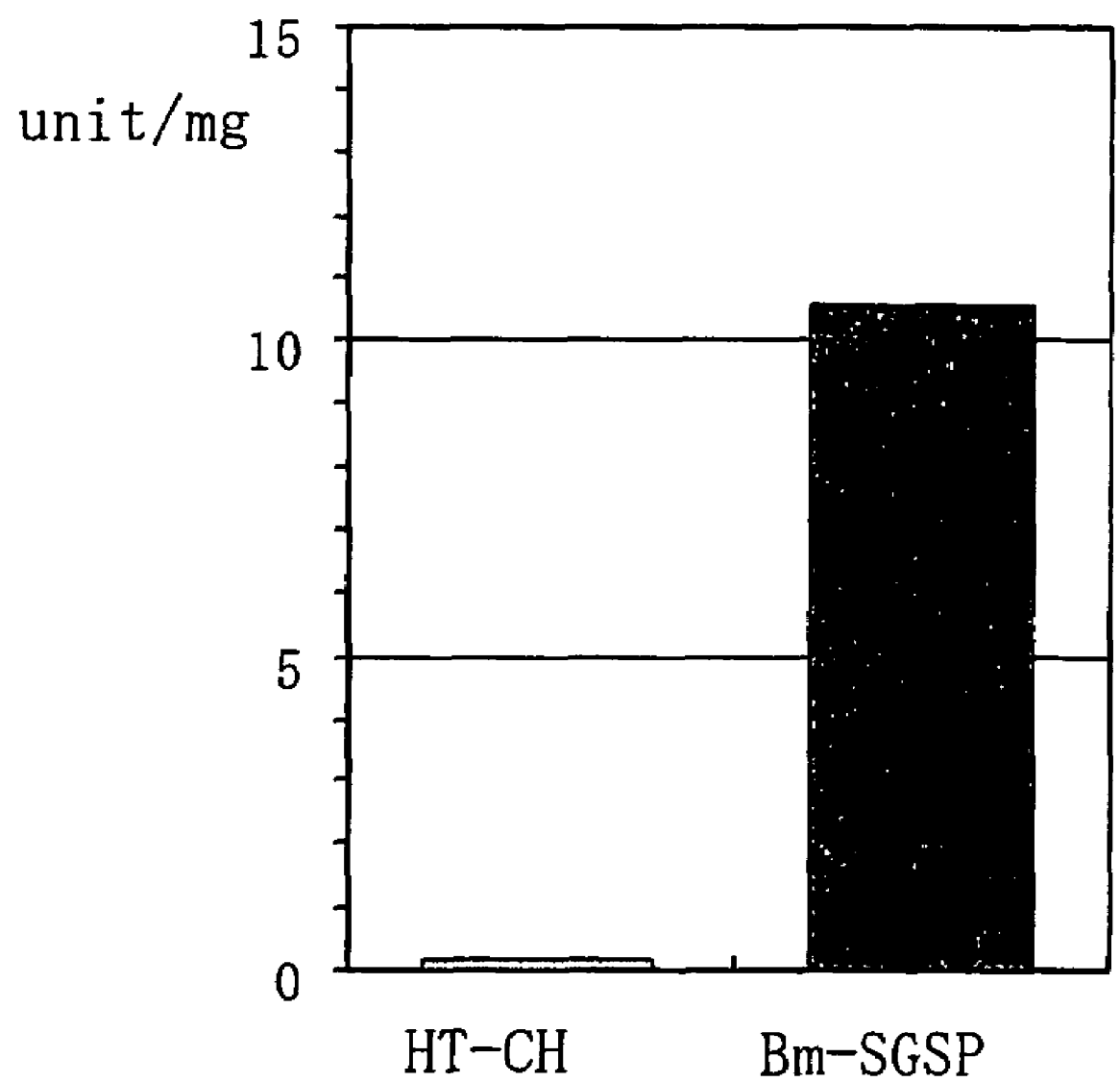
F I G. 7

PROTEIN AND DNA ENCODING THE SAME

This is a 371 of International Application PCT/JP02/01934 filed on Mar. 1, 2002, which designated the U.S., and claims the benefit thereof and incorporates the same by reference, said International Application PCT/JP02/01934 claiming priority to Japan Patent Application No. 2001-059057 filed Mar. 2, 2001.

BACKGROUND OF THE INVENTION

1. Field of the Invention

The present invention relates to a new protein derived from the middle silk gland of silkworm and a DNA encoding said protein.

2. Background Art

Conventionally, a large number of proteases are isolated from organisms, such as animals, plants, and microorganisms. They are used in a wide variety of fields, such as food processing, meat softening, leather industry, optical resolution, detergent additives, digestion or restrictive decomposition of proteins and peptides, analysis, identification, decomposition or synthesis of various peptides and proteins, and further, test reagents or pharmaceuticals for diseases.

As the range of the field for industrial use of proteases expands, there is a need for proteases which are highly stable and valuable for application in terms of substrate specificity or the like. Consequently, remodeling of proteases by so-called protein engineering or further search for new proteases of natural origin are in progress.

SUMMARY OF THE INVENTION

The present inventors have recently found a specific protein having protease activity, which is specifically present in a cell of silkworm, an industrially important insect, particularly in the silkworm silk gland. Further, the present inventors have recently cloned a DNA encoding this new protease which is dominantly expressed in the silkworm middle silk gland, determined a base sequence of this DNA sequence and an amino acid sequence estimated from this base sequence, and further, succeeded in expressing this DNA in a host for production. The expression product thus obtained had protease activity. This expression product was named Bm-SGSP (or "Bombyx mori silk gland-derived serine protease"). The present invention is based on these findings.

Accordingly, an object of the present invention is to provide a new protein derived from the silkworm middle silk gland, and a DNA encoding said protein.

The protein according to the present invention is selected from the group consisting of:

(a) a protein comprising the amino acid sequence represented by SEQ ID NO: 1;

(b) a protein comprising a modified amino acid sequence of the amino acid sequence described in (a) above, in which one or more amino acid residues are deleted, substituted, inserted or added, and having protease activity.

Here the amino acid sequence of SEQ ID NO: 1 is the following sequence.

(SEQ ID NO: 1):
MetCysLeuGluLeuValLeuValValLeuAlaLeuAsnGlyValLeu

SerGlnSerProGlyCysAspPheAlaGlnAsnIleAlaValGlyThr

ThrValAspIleSerSerProGlyTyrProGlyAsnTyr(Arg/Ser)

ProGlyIleGlnCysArgTrpIleAlaThrCys(Pro/Leu)ValGly

-continued
TyrAsnCysGlnIleAspCysProIleIleSerIleProGlnSerSer

SerCysIleAspArgLeuLeuLeuSerArgThrGlyAspProGlnLeu

SerGlyAlaGluValTyrCysGlyArgGlyThrLeuSerAlaThrSer

ValGlyGlnArgLeuSerLeuGlyLeuIleSerSerAsnSerSerPro

GlyGlyTyrPheArgCysArgValTyrAlaValAlaSerAlaProSer

ProAlaProCysArgCysGlyGluArgLysGlnThrArgIleValGly

GlyGluGluAlaLysIleAsnGluPheArgMetMetValGlyLeuVal

AspIleSerIleArgGlnIleLysCysGlyGlyAlaLeuIleSerAsn

ArgHisValLeuThrAlaAlaHisCysIleAlaAsnGlnArgThrAsp

AsnIleGlyValIleValGlyGluHisAspValSerSerGlyThrGlu

SerAlaAlaGlnGlyTyrValValGlnArgPheIleIleHisProLeu

PheThrAlaSerAsnTyrAspTyrAspValAlaIleValGluThrThr

LysGluIleThrPheSerAspIleValGlyProAlaCysLeuProPhe

LysPheValAsnThrAsnPheThrGlyLeuLysValThrIleLeuGly

TrpGlyThrLeuPheProGlyGlyProThrSerAsnValLeuArgLys

ValAspLeuAsp(Val/Ile)IleSerGlnSerThrCysArgSerTyr

GluSerThrLeuThrAspArgGlnMetCysThrPheThrProGlyLys

AspAlaCysGlnAspAspSerGlyGlyProLeuLeuTyrThrAspPro

SerThrGlyLeuPhePheAsnLeuGlyIleValSerTyrGlyArgPhe

CysAlaSerAsnSerProGlyIleAsnMetArgValThrAlaValLeu

AspTrpIleValSerSerThrGlnTyrAsnPheCysArgLys

[In the abovementioned sequence, amino acid residues in parentheses can be either one of them.]

Further, according to the present invention, there is provided a DNA coding the abovementioned protein (a) or (b). According to one preferred embodiment of the present invention, there is provided a DNA which comprises a base sequence having 60% or more homology to the base sequence represented by SEQ ID NO: 2 and has protease activity.

Here the base sequence of SEQ ID NO: 2 is the following sequence.

(SEQ ID NO: 2):
ATGTGCCTTGAACTTGTATTGGTTGT(A/G)CTGGCCTTGAA(T/C)GG

CGTGTTATCACAGAGCCCGGGATGCGACTT(T/C)GCGCAAAATATTGC

CGTCGGAACTACGGTGGATATAAGCAGTCCGGGTTACCCCGGCAACTAC (C/A)GTCCCGGTATTCAATGTAGATGGATAGCGACATGTC(C/T)CGT

TGGATACAATTGTCAAATAGATTGCCCCATAAT(C/A)TCCATACCCCA

AAGTTCTTCTTGCATAGATCGACTATTGCTCTC(A/G)AGGACGGGTGA

CCCCCAATTGAGTGGAGCCGAAGTCTACTGCGGGAGAGAACTTTATCT

GCAACTTCTGTTGGCCAGAGACTTAGTTTGGGGTTGATATCTTCAAACT

CAAGTCCCGGTGGATACTTCAGGTGTCGCGTATACGCGGTGGCATCAGC

TCCTAGTCCAGCACCTTGCAGATGCGGGAAAGGAAACAGACCCGCATT

GTGGGGGGTGAAGA(G/A)GC(G/T)AAAATCAATGAATTCCGAATGAT

-continued

```
GGTCGGGTTAGTTGATATCAGCATCAGGCAAATCAAATGCGGAGGCGCC

TTGATCTCTAATAG(A/G)CATGTACTGAC(C/T)GCAGCCCATTGTAT

TGCCAACCAAAGAACGGATAACATAGGAGTTATAGTTGGAGAACACGAT

GTTTCCAGCGGCACAGAATCGGCAGCTCAGGGTTACGTAGTACAAAGGT

TTATTATACATCCATTATTTACTGCTTCCAATTATGACTACGACGTGGC (G/C)ATAGTGGAAACAACAAAGGAAATAACATTCAGCGATATAGTTGG

ACCGGCTTGTCTACCGTTCAAGTTCGTCAATACCAATTTCACTGGCTTA

AAAGTTACCATTCTTGGTTGGGGAACGTTATTCCCGGGAGGTCCAACGT

CTAATGTTCTCCGTAAGGTAGACCTGGACGTCATCAGCCAGAGCACCTG

TAGGAGTTACGAGTCGACACTGACGGACAGACAGATGTGCACATTCACT

CCTGGGAAGGACGCGTGTCAAGACGACTCCGGTGGCCCTCTGCTCTATA

CAGACCCGAGTACCGGATTGTTCTTCAACCTGGGCATCGTGAGTTACGG

TCGTTTCTGCGCATCAAACAGTCCGGGCATCAACATGAGAGTCACCGCA

GTACTGGACTGGATCGTCTCGTCCACGCAATATAACTTCTGCAGGAAAT

AA
```

[In the abovementioned sequence, bases in parentheses can be either one of them.]

According to the present invention, a DNA encoding serine protease, particularly Bm-SGSP, expressed dominantly in the silkworm silk gland can be cloned and further a protein encoded by this DNA can be isolated and purified. The protein according to the present invention is very useful for analysis of protein structure or its functional alteration by cleaving specified amino acid sequences using substrate specificity, or for pharmaceuticals in which specific protein decomposition is targeted, or in various fields, such as or food processing, e.g., food softening and flavor improvement.

BRIEF DESCRIPTION OF THE DRAWINGS

FIG. 1 illustrates the relation between a conserved sequence of serine protease and primer set-up sequences.

FIG. 2 shows the steps of constructing a plasmid having the complete length of the silkworm silk gland serine protease gene.

FIG. 3a and FIG. 3b show the base sequence and amino acid sequence of Bm-SGSP.

FIG. 6 is a photograph demonstrating the result of electrophoresis for confirming production of Bm-SGSP by insect cells (Step 11 in Example).

FIG. 7 is the result of measurement of protease activity of Bm-SGSP.

DETAILED DESCRIPTION OF THE INVENTION

Protein According to the Present Invention

Figure 4:
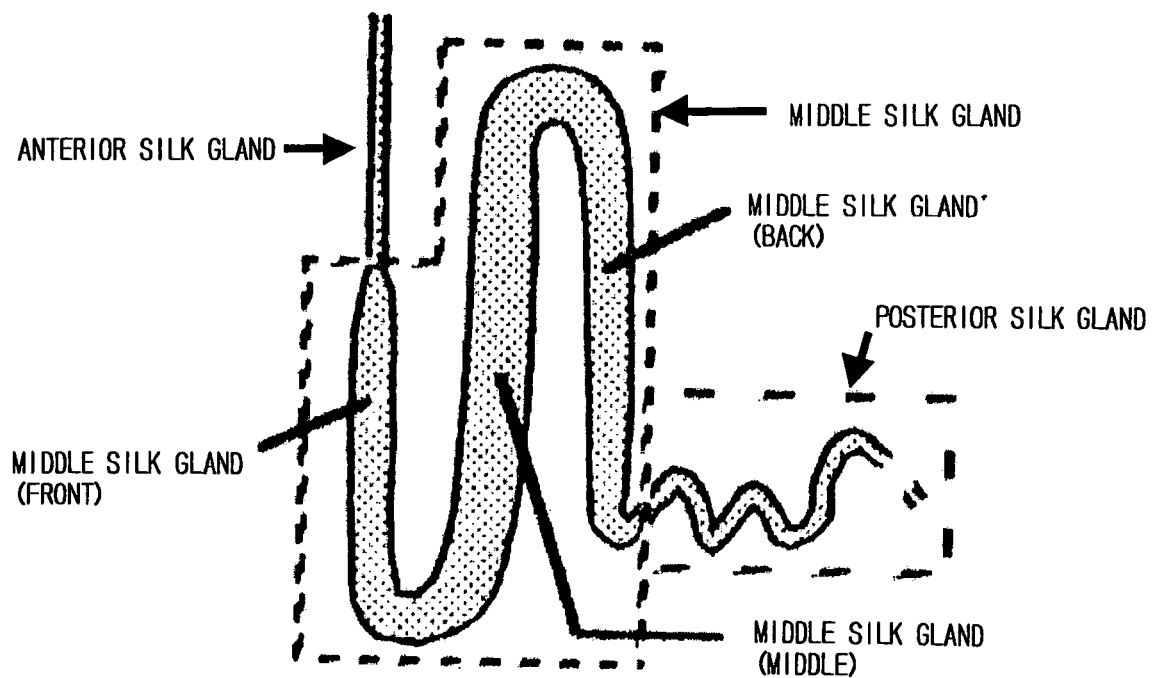
FIG. 4 illustrates the silkworm silk gland.

The protein according to the present invention is selected from the group consisting of:

(a) a protein comprising the amino acid sequence represented by SEQ ID NO: 1;

(b) a protein comprising a modified amino acid sequence of the amino acid sequence described in (a) above, in which one or more (preferably 1 to 24, more preferably 1 to 10, and most preferably 1 to 5) amino acid residues are deleted, substituted, inserted or added, and having protease activity.

In the present invention, a protein having protease activity means a protein which is recognized to have protease activity by skilled in the art. For example, it means a protein which is evaluated to have protease activity when measured under the same condition as described in Step 9 in Example.

In the present invention, protease activity of the protein is preferably serine protease activity. Namely, the protein according to the present invention is preferably silkworm silk gland-derived serine protease (Bm-SGSP).

Further, the protein according to the present invention includes a derivative of the protein. The derivative herein means any protein (peptide) having the above mentioned protease activity, in which the amino group of the amino terminus (N terminus) of the protein or a part or all of amino groups on its side chains of each amino acid, and/or the carboxyl group of the carboxyl terminus (C terminus) of the peptide or a part or all of carboxyl groups on its side chains of each amino acid, and/or a part or all of functional groups other than the amino groups and carboxyl groups on side chains of each amino acid (e.g., hydrogen group, thiol group, and amide group) are modified with appropriate substitution groups. Such modifications by other appropriate substitution groups are occasionally used for the purpose of blocking functional groups present in a peptide, and improving safety and tissue mobility, or enhancing activity.

In the present invention, the term "amino acid" implies its optical isomers, namely both D and L forms. Further the amino acid herein may imply not only 20 kinds of α-amino acids which construct natural proteins but also other α-amino acids as well as β-, γ- and δ-amino acids and nonnatural amino acids.

In a more preferred embodiment of the present invention, the protein of the abovementioned (b) is a protein comprising a modified amino acid sequence of the amino acid sequence described in (a) above, in which one or more amino acid residues are conservatively substituted, and having protease activity.

The term "conservative substitution" herein means substitution of one or more amino acid residues with other chemically homologous amino acid residues without substantially changing protein activity. For example, a certain hydrophobic residue can be substituted with another hydrophobic residue, a certain polar residue can be substituted with another polar residue having the same charge, or a certain aromatic amino acid can be substituted with another aromatic amino acid. Functionally homologous amino acids which can be conservatively substituted in such a manner are known in the art for individual amino acids. The following six groups are specific examples. The amino acids in the same group can be conservatively substituted with each other.

(i) Alanine (Ala), serine (Ser) and threonine (Thr)
(ii) Aspartic acid (Asp) and glutamic acid (Glu)
(iii) Asparagine (Asn) and glutamine (Gln)
(iv) Arginine (Arg) and lysine (Lys)
(v) Isoleucine (Ile), leucine (Leu), methionine (Met), and valine (Val)
(vi) Phenylalanine (Phe), tyrosine (Tyr), and tryptophan (Trp)

According to another preferred embodiment of the present invention, there is provided a protein which comprises an amino acid sequence having 55% or more homology to a protein consisting of the amino acid sequence represented by SEQ ID NO: 1 and has protease activity. The abovementioned homology is 55% or more, preferably 60% or more, and more preferably 70% or more.

The level of "homology" herein can be determined by comparison with the amino acid sequence represented by SEQ ID NO: 1, for example using a homology search program BLAST (Basic Local Alignment Search Tool) (developed by NCBI (National Center for Biotechnology Information and available via internet) or genetic information process software GENETYX (Software Development Co.).

According to a more preferred embodiment, the protein according to the present invention comprises the following (a') or (b'):

(a') a protein comprising the amino acid sequence represented by SEQ ID NO: 3;

(b') a protein comprising a modified amino acid sequence of the amino acid sequence described in (a) above, in which one or more (preferably 1 to 24, more preferably 1 to 10, and most preferably 1 to 5) amino acid residues are deleted, substituted, inserted or added, and having protease activity.

DNA According to the Present Invention

A DNA according to the present invention is a DNA encoding the abovementioned protein. Accordingly, the DNA according to the present invention is a DNA encoding a protein of the following (a) or (b):

(a) a protein comprising the amino acid sequence represented by SEQ ID NO: 1;

(b) a protein comprising a modified amino acid sequence of the amino acid sequence described in (a) above, in which one or more amino acid residues are deleted, substituted, inserted or added, and having protease activity.

Generally, given an amino acid sequence of a protein, a base sequence encoding it can be easily determined referring to the so-called codon table. Accordingly, various base sequences encoding the amino acid sequence represented by SEQ ID NO: 1 can be appropriately selected. Accordingly, in the present invention, the DNA encoding the protein comprising the amino acid sequence of SEQ ID NO: 1 implies the DNA having the base sequence represented by SEQ ID NO: 2 as well as any DNA encoding the same amino acid sequence of said SEQ ID NO: 1 having degenerative codons in the base sequence.

According to one preferred embodiment of the present invention, a DNA of the present invention comprises a base sequence having 60% or more homology to a DNA comprising the base sequence represented by SEQ ID NO: 2 and encodes a protein having protease activity. The abovementioned homology is 60% or more, preferably 70% or more, more preferably 80% or more, and most preferably 90% or more.

In the present invention, DNA mutants can be prepared from the DNA comprising the base sequence of SEQ ID NO: 2 by methods known in the art, for example, by site specific mutation induction, point mutation, deletion, overlap, inversion, insertion, translocation, and conservative alteration in which only base sequences are changed using degeneration of gene codes without changing amino acid sequences.

According to another preferred embodiment of the present invention, a DNA of the present invention is a DNA which hybridizes with a DNA comprising the base sequence represented by SEQ ID NO: 2 under stringent conditions and encodes a protein having protease activity.

According to a preferred embodiment of the present invention, a DNA of the present invention comprises the base sequence represented by SEQ ID NO: 2, and more preferably the base sequence represented by SEQ ID NO: 3.

Preparation of Protein

The protein according to the present invention can be either produced using various ordinary synthesizing methods or derived from natural origin. This protein according to the present invention can be obtained entirely by synthesis or can be obtained by using a partial sequence of a naturally derived sequence and further synthesizing based on the partial sequence, since its amino acid sequence is determined. According to one embodiment of the present invention, the protein according to the present invention can be derived from a natural silkworm middle silk gland.

Further, if a DNA encoding a protein according to the present invention is available or can be constructed, the protein can be produced in transformed cells obtained by transforming host cells with such a DNA. More specifically, the protein according to the present invention can be produced by obtaining a DNA, in particular in a form of a recombinant vector, which is replicable in a host cell and includes a DNA fragment encoding the protein in an expressible state, transforming the host cell using the DNA or the vector and culturing the transformed cell thus obtained. Namely, in the present invention, a so-called host-vector system can be used for the production of said protein. In the present invention, for applying such a host-vector system, various conventional methods used in this field of technology can be used for the construction of expression vectors (recombinant vectors) and transformation.

Accordingly, according to another embodiment of the present invention, there is provided a method of producing a protein according to the present invention comprising the steps of culturing the abovementioned transformed cells and recovering the protein of interest from the resulting cells and/or cell culture. Further, according to another preferred embodiment of the present invention, the protein according to the present invention is a protein produced by the above-mentioned method.

Recombinant Vector

According to the present invention, there is provided a recombinant vector comprising a DNA encoding a protein according to the present invention.

Such a vector can be obtained by incorporating a DNA fragment encoding a protein of the present invention into a conventional vector system. In the present invention, this vector can include at least 2 repeats of the abovementioned DNA fragment.

The vector to be used in the present invention can be appropriately selected from conventional vectors for which the host-vector system has been established, such as plasmids, viruses, artificial chromosomes, phages, and cosmid vectors, taking the kind of the host cell to be used into consideration. More specifically, for example, pBR, pUC or pQE plasmids, or λ-phage bacteriophages can be used when *Escherichia coli* is used as a host cell, pUB plasmids can be used for *Bacillus subtilis*, YEp or YCp vectors can be used for yeasts, and pSV2dhfr having a primary promoter of SV 40 (see Subramani, S. et al., Mol. Cell. Biol. 1, 854-864 (1981)) can be used for vertebrate animal cells. An example of the vector for plants is pBI121 which has the primary promoter of the cauliflower mosaic virus, i.e., the 35s promoter, and a polyadenylated sequence of the nopaline synthesis gene of *Agrobacterium tumefaciens* as well as the gene transfer sequence for *Agrobacterium tumefaciens* (see Jefferson, R. A. et al., EMBO J. 6, 3901-3907 (1987)). The vector to be used in the present invention is preferably a plasmid.

In the present invention, the vector can contain one or more selective markers to select a transformed cell which is transfected or transformed with the DNA of the present invention. Examples of such selective markers include a resistance gene to antibiotics such as kanamycin, chloramphenicol, tetracycline, and neomycin, a gene complimenting a nutritional requirement, and control by a cell death associated gene.

Further, the recombinant vector according to the present invention is preferably a vector in which DNAs necessary for the expression of the abovementioned protein, e.g., a promoter or other regulatory sequences (e.g., a ribosome binding site, polyadenylation signal, transcription promoter, transcription termination sequence, translation stop signal, upstream regulatory region, enhancer, operator, and signal sequence, for bacterial expression) are ligated to the DNA of the present invention.

Here, the promoter or other regulatory sequences are not particularly limited and any sequences known to the skilled in the art can be used as long as the DNA of the present invention can be expressed. Examples of such sequences include lacpromoter, T7 promoter, trp promoter, tac promoter, SV40 promoter, CMV promoter, retrovirus LTR, EF promoter, and a part of these promoters. The recombinant vector can contain a regulatory sequence which controls protein expression, in addition to the abovementioned regulatory sequences.

Transformed Cell

According to the present invention, there is provided a transformed cell which is created by transfecting or transforming a host cell with the abovementioned recombinant vector.

A host cell to be used in the present invention can be any cell for which the host-vector system has been established. Such a host cell can be either a prokaryotic or eukaryotic cell.

In the present invention, examples of the prokaryotic cell to be used as a host cell include *Escherichia coli* and *Bacillus subtilis*. In order to express the DNA of interest in such a host cell, the host cell can be transformed with a plasmid vector containing a replication origin and a promoter sequence which are compatible with the host.

For example, the *E. coli* K12-derived JM109 strain is often used as an *E. coli* host and in such a case, a pBR322 or pUC plasmid can generally be used as a recombinant vector. However, these are not intended as a limitation of the present invention and various known strains and vectors can be used. Examples of the promoter in *E. coli* include the lactose promoter (lac) and the tryptophan/lactose promoter (trc).

In the present invention, examples of the eukaryotic cell to be used as a host cell include cells of vertebrate animals, insects, yeasts, fungi, and plants.

Examples of the vertebrate animal cells include monkey COS cells (see Gluzman, Y., Cell 23, 175-182 (1981)), human kidney germ cells, and CHO cells.

Examples of the insect cells include cells derived from fall armyworm of the family Noctuidae, *Spodoptera frugiperda* (see Smith, G. E. et al., Mol. Cell. Biol. 3, 2156-2165 (1983)), and *Drosophila* cells. Bodies such as silkworms can also be used.

Examples of the yeasts include Baker's yeast (*Saccharomyces cerevisiae*) and fission yeast (*Schizosaccharomyces pombe*).

Examples of the plant cells include tobacco plant (*Nicotiana tabacum*) cells and rice plant (*Oryza sativa*) cells.

In the present invention, cells to be used as a host cell are preferably eukaryotic cells. Preferable eukaryotic cells are, for example, hamster-derived CHO cells, yeast cells, and insect cells.

In a more preferred embodiment of the present invention, the host cell is an insect cell. Insect cells can advantageously be used in the present invention because they are easy to handle, well known in the art, can easily be cultured on a large scale for mass production of a DNA or protein of interest, and further allows the protein of interest to fold correctly.

An example of such an insect cell is an insect cell of the family Noctuidae, *Spodoptera frugiperda*, for which the baculovirus expression system is known. An example of the insect cell of the family Noctuidae is an established cell line Sf9 cell (Invitrogen) from an oocyte of *Spodoptera frugiperda* belonging to the family Noctuidae.

Protein Purification

The protein according to the present invention obtained by the abovementioned method can be recovered using its chemical or physical characteristics and isolated and purified appropriately using various ordinary isolation methods. For example, the protein according to the present invention can be isolated and purified by treatment with a protein coagulant, ultrafiltration, adsorption chromatography, ion-exchange chromatography, affinity chromatography, molecular sieving chromatography, dialysis and the like, singly or in combination.

EXAMPLE

The present invention is further illustrated by the following examples that are not intended as a limitation of the invention.

Step 1: Preparation of Total RNA from Silkworm Middle Silk Gland

The silk glands of silkworm mature larvae 4 days after molting were excised to prepare the total RNA using a TRIZOL reagent (Life Technologies Oriental, Inc.). The silkworm used was a generally available domestic silkworm *Bombyx mori*.

Step 2: Designing and Synthesis of Primers for cDNA Synthesis

A characteristic conserved sequence is present in various serine proteases. Based on this sequence, 3 different degenerate PCR primers, namely, the following primer 1, primer 2 and primer 3 were designed and chemically synthesized by the phosphoamidite method using a DNA synthesizer.

The conserved sequence of serine protease and positions of the primers are shown in FIG. 1.

Synthesized Primers

```
primer 1: 5'-GTNBTNWCNGCNGCNCAYTG-3'  (SEQ ID NO: 4)

primer 2: 5'-AVNGGNCCNCCNGARTCNCC-3'  (SEQ ID NO: 5)

primer 3: 5'-CCNGARTCNCCNTKRCANG-3'   (SEQ ID NO: 6)
```

In the sequences above,
N represents A, C, G or T,
B represents C, G or T,
V represents A, C or G,
W represents A or T,
Y represents C or T,
R represents A or G, and
K represents G or T.

Step 3: Preparation of cDNA by RT-PCR (Reverse Transcription-Polymerase Chain Reaction) Method A cDNA was synthesized from the total RNA of the silkworm middle silk gland prepared in Step 1, using primer 2 synthesized in Step 2 and Super Script™ II RNase H⁻ reverse transcriptase (Life Technologies Oriental, Inc.).

The reaction was carried out as follows. The reaction mixture containing the total RNA and the primer was incubated at 70° C. for 10 minutes and then at 37° C. for 2 minutes, after which Superscript II RNase H⁻ reverse transcriptase was added to carry out the reverse transcription reaction at 37° C. for 1 hour.

Step 4: Screening of cDNA Encoding Partial Protein of Serine Protease

The first PCR was carried out with primer 1 and primer 2 synthesized in Step 2 above, using the cDNA obtained in Step 3 as a template. The reaction conditions were incubation at 94° C. for 2 minutes, followed by DNA amplification for 30 cycles, each cycle consisting of incubations at 94° C. for 30 seconds, 55° C. for 30 seconds, and 72° C. for 1 minute.

Next, the second PCR was carried out with primer 1 and primer 3 synthesized in Step 2 above, using the first PCR product as a template.

The conditions for this reaction were incubation at 94° C. for 2 minutes, followed by DNA amplification for 30 cycles, each cycle consisting of incubations at 94° C. for 30 seconds, 55° C. for 30 seconds, and 72° C. for 1 minute.

An equivalent of TE saturated phenol was added to a sample of the reaction solution obtained by the PCR above and the admixture was thoroughly mixed and then centrifuged (12,000 g×, 5 minutes) (phenol treatment). The resulting supernatant was then recovered and treated with chloroform to remove phenol. Further, 0.1×sample volume of 5 M ammonium acetate and 2.5×sample volume of ethanol were added and then the admixture was centrifuged (12,000 g ×, 30 minutes) to recover DNA (ethanol precipitation).

The PCR product thus obtained was dissolved in a TE buffer solution.

Step 5: Cloning of PCR Product

The PCR product was subjected to agarose gel electrophoresis and a band for the amplified DNA of about 0.47 kbp was excised and recovered. The DNA fragment thus obtained was subcloned into pGEM-T plasmid (Promega, Inc.) by the TA cloning method to obtain a recombinant vector.

An *E. coli* JM109 strain was transformed with the recombinant vector thus obtained. Next, the resulting *E. coli* cells were spread on an LB agar medium supplemented with ampicillin and incubated at 37° C. overnight. *E. coli* colonies grown on the LB agar medium supplemented with ampicillin were selected and a plasmid was prepared from transformed *E. coli* cells by the ordinary method.

Next, a base sequence of the DNA inserted into the plasmid thus obtained was determined. The sequencing reaction was carried out with 2 different sequence primers shown below (T7 Primer and SP6 primer) using ThermoSequenase™ Dye Terminator Cycle Sequencing Kit V. 2.0 (Amersham, Inc.). The reaction conditions were incubation at 96° C. for 1 minute, followed by 25 reaction cycles, each consisting of incubations at 96° C. for 30 seconds, 50° C. for 15 seconds, and 60° C. for 4 minutes.

Primers

```
T7 Primer:
5'-TAATACGACTCACTATAGGGCGA-3'     (SEQ ID NO: 7)

SP6 Primer:
5'-ATTTAGGTGACACTATAGAATAC-3'    (SEQ ID NO: 8)
```

The PCR product thus obtained was subjected to sequencing by a DNA auto sequencer (PRISM™ Model 377, ABI, Inc.), which confirmed a cDNA sequence presumably encoding a new serine protease.

Step 6: Cloning of 5'-terminal cDNA of Silkworm Serine Protease by 5' RACE (Rapid Amplification of cDNA Ends) Method Sequences of 5 different primers used were as follows:

Primer Sequences

```
GSP1-L Primer:
5'-CCACGTCGTAGTCATAATTG-3'       (SEQ ID NO: 9)

GSP2-L Primer:
5'-TAACCCTGAGCTGCCGATGCTGT-3'    (SEQ ID NO: 10)

GSP3-L Primer:
5'-GCTGGAAACATCGTGTTCTCCAA-3'    (SEQ ID NO: 11)
```

Abridge Universal Amplification Primer (AUAP):

```
5'- GGCCACGCGTCGACTAGTAC -3'     (SEQ ID NO: 12)
```

Abridged Anchor Primer:

```
                                 (SEQ ID NO: 13)
5'-GGCCACGCGTCGACTAGTACGGGIIGGGIIGGGIIG-3'
```

The total RNA prepared from the silkworm middle silk gland as described in Step 1 was subjected to the reverse transcription reaction using the abovementioned primer GSP1-L as described in Step 3 to synthesize a cDNA.

Next, the 5'-terminal cDNA was cloned using a 5' RACE system (5' Race System for Rapid Amplification of cDNA Ends, Version 2.0; Life Technologies Oriental, Inc.).

Primers used for the first PCR were the Abridged Anchor Primer and GSP2-L. The conditions for the PCR reaction were incubation at 94° C. for 5 minutes, followed by DNA amplification for 30 cycles, each consisting of incubations at 94° C. for 1 minute, 55° C. for 30 seconds, and 72° C. for 3 minutes.

The second PCR was carried out with primers AUAP and GSP3-L using the product obtained by the first PCR as a template. The conditions for the PCR reaction were incubation at 94° C. for 5 minutes, followed by DNA amplification for 30 cycles, each consisting of incubations at 94° C. for 1 minute, 55° C. for 30 seconds, and 72° C. for 3 minutes.

Agarose gel electrophoresis of the PCR product thus obtained confirmed the amplification of several bands, among which a band of about 0.75 kbp was dominant.

The DNA fragment of about 0.75 kbp was recovered in the same manner as described in Step 4, and further, the recovered PCR product was inserted into pBluescript II SK plasmid as described in Step 5, after which transformation and DNA autosequencing were carried out.

Step 7: Cloning of 3'-terminal cDNA of Silkworm Serine Protease by 3' RACE Method Sequences of 4 different primers used were as follows:

Primer Sequences

```
GSP1-U Primer:
5'-TTCTTGGTTGGGGAACGTTATTC-3'    (SEQ ID NO: 14)

GSP2-U Primer:
5'-ACGTCTAATGTTCTCCGTAAGGT-3'    (SEQ ID NO: 15)

AUAP:
5'-GGCCACGCGTCGACTAGTAC-3'       (SEQ ID NO: 16)
```

3' RACE Adapter Primer:

(SEQ ID NO: 17)
5'- GGCCACGCGTCGACTAGTACTTTTTTTTTTTTTTTTT -3'

The total RNA prepared from the silkworm middle silk gland as described in Step 1 was subjected to the reverse transcription reaction using the abovementioned 3' RACE Adapter Primer as described in Step 3 to synthesize a cDNA.

Next, the first PCR was carried out with primers GSP1-U and AUAP using the cDNA obtained as described above as a template. The conditions for the PCR reactions were incubation at 94° C. for 5 minutes, followed by DNA amplification for 30 cycles, each consisting of incubations at 94° C. for 1 minute, 55° C. for 30 seconds, and 72° C. for 3 minutes.

The second PCR was carried out with primers GSP2-U and AUAP using the PCR product obtained by the first PCR as a template. The conditions for the PCR reaction were incubation at 94° C. for 5 minutes, followed by DNA amplification for 30 cycles, each consisting of incubations at 94° C. for 1 minute, 55° C. for 30 seconds, and 72° C. for 3 minutes.

Agarose gel electrophoresis of the PCR product thus obtained confirmed the amplification of several bands, among which a band of about 0.45 kbp was dominant.

The amplified DNA fragment of about 0.45 kbp was recovered in the same manner as described in Step 4, and further, the recovered PCR product was inserted into pBluescript II SK⁻ plasmid as described in Step 5, after which transformation and DNA autosequencing were carried out.

As a result of sequencing, multiple 5' RACE and 3' RACE clones which overlap with the cDNA clone obtained in Step 5 above were obtained. It was revealed from the predicted amino acid sequence encoded by this DNA, that the new serine protease derived from the silkworm silk gland comprises 392 amino acids encoded by the DNA of 1,179 bp in total length from the start codon to the stop codon.

Step 8: Acquisition of Total Length of cDNA Clone of Silkworm Silk Gland Serine Protease A complete length of the silkworm silk gland serine protease cDNA was acquired from the cDNA fragment resulted from the 5' RACE and 3' RACE, as follows.

FIG. 2 illustrates the general steps of acquiring the total length of the cDNA clone.

For PCR amplification of the cDNA encoding the complete length of silkworm silk gland serine protease, specific PCR primers (SGSP-5-Rsr and SGSP-3-Hind) were designed based on the start codon and the stop codon revealed in Step 6 and Step 7 and chemically synthesized according to the ordinary method. Sequences of the primers are as follows.

Primer Sequences

```
SGSP-5-Rsr Primer:  5'-TCTCGGTCCGTCAGAAATGTGCCTTGAACTTGTA-3'   (SEQ ID NO: 18)

SGSP-3-Hind Primer: 5'-CCAAGCTTATTTCCTGCAGAAGTTATATTGCG-3'     (SEQ ID NO: 19)
```

Next, in the same manner as described in Step 3, PCR was carried out with the abovementioned primers (SGSP-5-Rsr and SGSP-3-Hind) using the silkworm middle silk gland-derived cDNA as a prepared template DNA.

The resulting PCR product was subjected to agarose gel electrophoresis, which confirmed the amplification of a band of about 1.2 kbp.

The amplified DNA fragment of about 1.2 kbp was recovered as described in Step 4 above.

The PCR product obtained as descried above was subcloned into restriction sites (RsrII and HindIII) of the transfer vector HT-CH for baculovirus. The resulting transfer plasmid for baculovirus ligating the Bm-SGSP gene is herein referred to as pBm-SGSP.

DNA autosequencing confirmed that pBm-SGSP had the cDNA of the complete length of silkworm silk gland serine protease.

The base sequence and amino acid sequence of the complete length of the cDNA thus cloned are shown in FIG. 3.

The total length of the clone was 1,179 bp in length and coded for a protein consisting of 392 amino acid residues, which had a character of serine protease having residues such as His, Asp, and Ser in the active center. Further, a highly hydrophobic sequence, presumably a signal peptide, was found on the N-terminal side.

Step 9: Confirmation of Expression of Silkworm Silk Gland Serine Protease in Different Sections of Silk Gland by RT-PCR Method Next, expression of silkworm silk gland serine protease in different sections of the silk gland was confirmed by the RT-PCR method. The total RNA was prepared from each section of the anterior silk gland, middle silk gland (front, middle and back parts), and posterior silk gland of silkworm mature larvae 4 days after molting, in the same manner as described in Step 1.

FIG. 4 shows each section of the silk gland.

Next, the reverse transcription reaction was carried out using the total RNA prepared from the each section of the silk gland and the abovementioned primer (3' RACE Adapter Primer) as described in Step 3 to synthesize a cDNA. PCR was then carried out using 4 μl of this cDNA sample and the primers synthesized in Step 8 (SGSP-5-Rsr and SGSP-3-Hind, 200 pmol each). The conditions for the PCR were 30 cycles, each consisting of incubations at 94° C. for 30 seconds, 55° C. for 30 seconds, and 72° C. for 2 minutes. The resulting sample was subjected to agarose gel electrophoresis to confirm the amplification.

Figure 5:
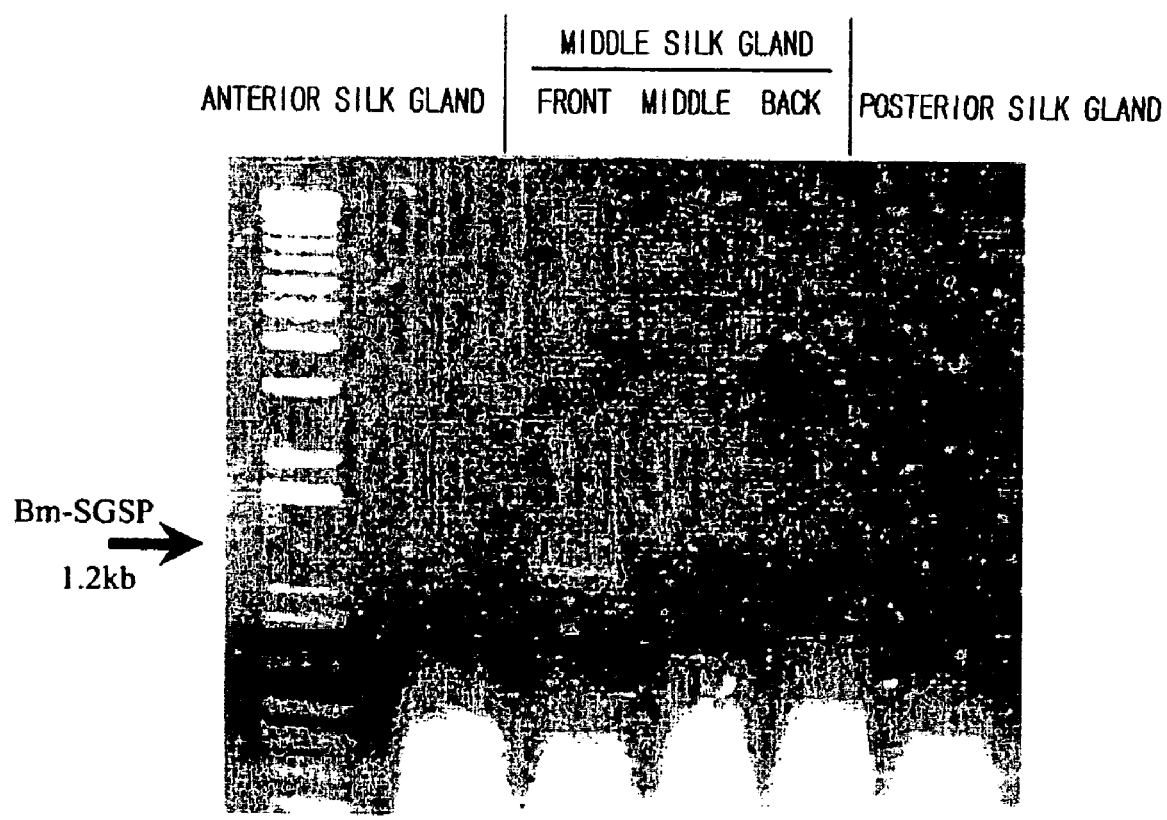
FIG. 5 is a photograph demonstrating the result of electrophoresis for confirming Bm-SGSP site-specific expression (Step 9 in Example).

The result is shown in FIG. 5.

FIG. 5 shows that Bm-SGSP was expressed dominantly in the middle section of the silkworm silk gland.

Step 10: Secretory Production of Bm-SGSP Using Insect Cell (Sf9)

Baculovirus (Life Technologies Oriental, Inc.) was used for protein production in insect cells.

*E. coli* DH10Bac carrying AcNPV virus DNA in the cell was transformed with the transfer vector for baculovirus containing the Bm-SGSP gene constructed in Step 8 above (pBm-SGSP), by the ordinary method.

Homologous recombination takes place in the transformed *E. coli* cells and thus the Bm-SGSP gene is incorporated into the AcNPV virus DNA. The lacZ gene is present in the AcNPV virus DNA in the DH10Bac, so that when incubated on a medium supplemented with X-gal (50 ng/ml), cells without homologous recombination form blue colonies while cells with homologous recombination, which destroys the lacZ gene, form white colonies.

Accordingly, white colonies were selected to prepare a recombinant virus DNA by the ordinary method.

Next, the virus DNA thus prepared was used for transfection of the insect cell Sf9 (cell derived from *Spodoptera frugiperda* of the family Noctuidae; available from Invitrogen).

The Sf9 cells ($2 \times 10^6$ cells/ml) were cultured in a Petri dish using SF900II SFM (+10% FCS) medium and after 4 days, the culture supernatant was recovered to obtain a virus fluid. Using this virus fluid ($1 \times 10^9$ pfu/ml), the Sf9 cells were further transfected with the baculoviruses, into which the Bm-SGSP gene was recombined, and incubated at 27° C. for 4 days to obtain 30 ml of a culture supernatant.

Step 11: Purification of Recombinant Bm-SGSP Protein Expressed in Insect Cells

The culture supernatant was dialyzed overnight against dialysis buffer (20 mM Tris (pH 8.5), 100 mM NaCl, 1 mM $CaCl_2$). In this experiment, Bm-SGSP excreted into the culture supernatant has a His-tag consisting of 6 histidines on its C-terminal side. Therefore, purification of the Bm-SGSP from the culture supernatant after dialysis was carried out using a Ni-NTA column (Ni-NTA Protein Purification System; Qiagen, Inc.) having a high affinity with the His-tag. The Bm-SGSP protein adsorbed on Ni-NTA (nickel-nitrile triacetic acid) was eluted with a 100 mM imidazole solution. A portion (1 µg) of the purified protein thus eluted was subjected to SDS-polyacrylamidegel electrophoresis to confirm the purified protein.

Figure 6:
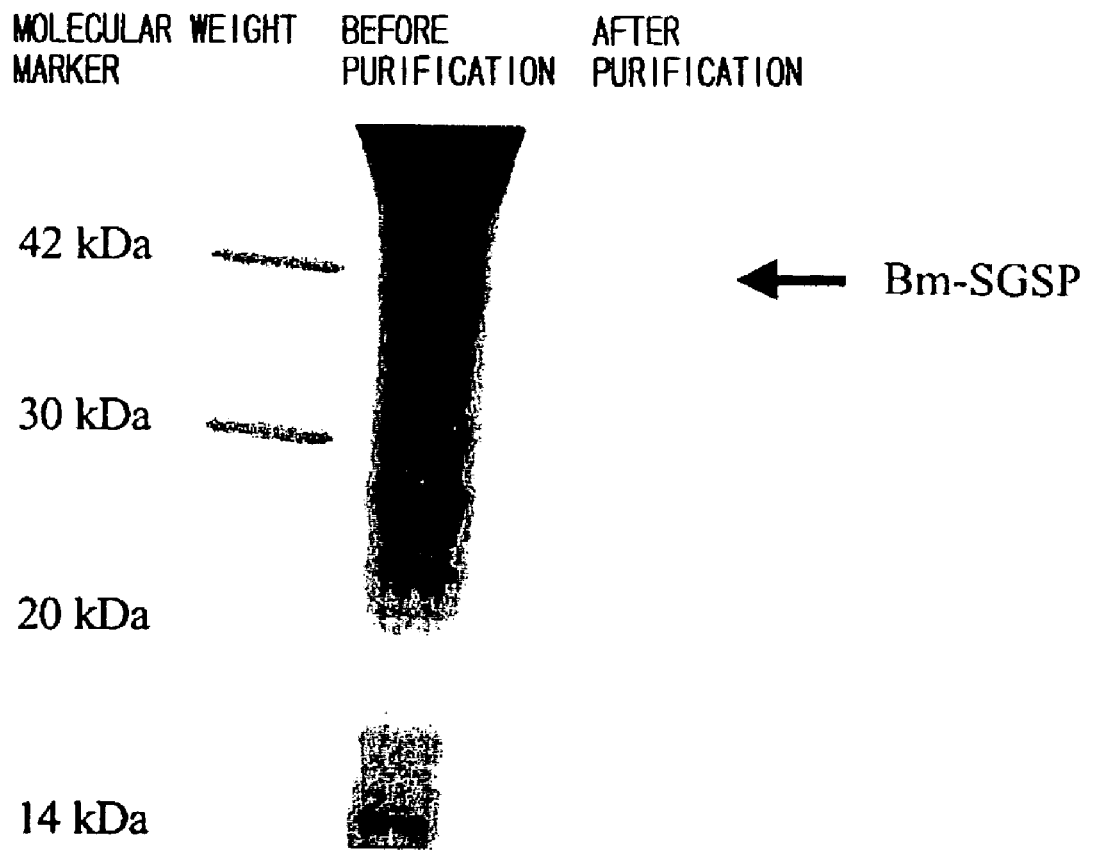

FIG. 6 shows the result of SDS-polyacrylamide gel electrophoresis.

After SDS-polyacrylamide gel electrophoresis, the purity of the protein was determined by silver staining of the gel. As shown in FIG. 6, the complete purification of the Bm-SGSP protein having a molecular weight of about 42 kDa from the culture supernatant of the Bm-SGSP cells was confirmed.

From 30 ml of the insect cell culture, 28.0 µg of the purified Bm-SGSP protein was obtained.

Step 12: Determination of Protease Activity of Silkworm-Derived New Serine Protease Bm-SGSP Protease activity was determined using a synthesized substrate which a trypsin-type serine protease specifically cleaves, i.e., succinyl-L-Ala-L-Ala-L-Pro-L-Lys-P-nitroanilide (or represented by "Suc-AAPK-pNA").

A culture fluid of Sf9 cells producing Bm-SGSP was centrifuged (15,000 rpm, 10 minutes) to obtain a cell fraction. Then, the cells were suspended in 10 mM Tris buffer (pH 7.5) and the suspension was treated with ultrasound to prepare a fluid with ruptured cells. The resulting fluid with ruptured cells was centrifuged (15,000 rpm, 10 minutes) to recover the supernatant, and thus an enzyme solution was obtained.

In a control experiment, the same steps were carried out using the Sf9 cell (HT-CH) producing no Bm-SGSP.

A mixture of 5 µl of 10 mM substrate (Suc-AAPK-pNA), 345 µl of 1 mM $CaCl_2$, and 375 µl of a buffer solution (50 mM piperazine-N,N'-bis (2-ethanesulfonic acid), 2 mM $CaCl_2$, pH 6.0) was incubated at 37° C. for 15 minutes. Next, 25 µl of the Bm-SGSP enzyme solution prepared as described above was added and the reaction was carried out at 37° C. for 150 minutes. After the reaction was completed, enzyme activity (U/mg) was determined by measuring optical density (410 nm) according to the ordinary method.

The result is shown in FIG. 7.

Here 1 U is the amount of enzyme necessary for releasing 1 nmol of p-nitroaniline per 1 minute. Molecular absorption coefficient at 410 nm for p-nitroaniline is 8900 ($M^{-1}$ $cm^{-1}$). Accordingly, the enzyme activity is obtained by the following formula:

$$U/mg = \Delta A410 \div (8.9 \times X \times Y \times Z) \times 10^6$$

wherein U/mg is enzyme activity per 1 mg of protein (unit/mg), $\Delta A410$ is change in optical density at 410 nm, X is the volume of enzyme solution (µl), Y is reaction time (minute), and Z is protein concentration (mg/ml).

As shown in FIG. 7, the silkworm silk gland-derived Bm-SGSP acquired in the present invention was confirmed to have serine protease activity since it cleaved a substrate Suc-AAPK-pNA which is specifically cleaved by a trypsin-type serine protease. The HT-CH is a negative control.

The invention claimed is:

1. An isolated protein selected from the group consisting of:
   (a) a protein comprising the amino acid sequence of SEQ ID NO:1; and
   (b) a protein comprising the amino acid sequence of SEQ ID NO:1, wherein no more than 1 to 10 amino acids are deleted, substituted, or inserted in the amino acid sequence of SEQ ID NO: 1,
   and wherein the protein has protease activity with the substrate Suc-AAPK-pNA.

2. An isolated deoxyribonucleic acid comprising a nucleic acid sequence encoding the protein of claim 1.

3. The isolated deoxyribonucleic acid according to claim 2, comprising the nucleic acid sequence of SEQ ID NO:2.

4. The isolated deoxyribonucleic acid according to claim 2, comprising the nucleic acid base sequence of SEQ ID NO:3.

5. A recombinant vector comprising the isolated deoxyribonucleic acid of claim 2.

6. A transformed host cell comprising the recombinant vector of claim 5.

7. The transformed host cell according to claim 6, wherein said transformed cell is an eukaryotic cell.

8. The transformed eukaryotic host cell according to claim 7, wherein said eukaryotic cell is an insect cell.

9. A method of producing a protein selected from the group consisting of:
   (a) a protein comprising the amino acid sequence of SEQ ID NO: 1; and
   b) a protein comprising the amino acid sequence of SEQ ID NO:1, wherein no more than 1 to 10 amino acids are deleted, substituted, or inserted in the amino acid sequence of SEQ ID NO:1,
   wherein the protein has protease activity with the substrate Suc-AAPK-pNA, and wherein the method comprises the steps of culturing the transformed cell of claim 6 and recovering the protein from the resulting cells, cell culture, or both.

* * * * *

SEQUENCE LISTING

<160> NUMBER OF SEQ ID NOS: 20

<210> SEQ ID NO 1
<211> LENGTH: 392
<212> TYPE: PRT
<213> ORGANISM: Bombyx mori
<220> FEATURE:
<221> NAME/KEY: MISC_FEATURE
<223> OTHER INFORMATION: The Xaa at the 46th positoin of the amino acid
      sequence is Arg or Ser
<220> FEATURE:
<221> NAME/KEY: MISC_FEATURE
<223> OTHER INFORMATION: The Xaa at the 57th positoin of the amino acid
      sequence is Pro or Leu
<220> FEATURE:
<221> NAME/KEY: MISC_FEATURE
<223> OTHER INFORMATION: The Xaa at the 305th positoin of the amino acid
      sequence is Val or Lle
<220> FEATURE:
<221> NAME/KEY: misc_feature
<222> LOCATION: (46)..(46)
<223> OTHER INFORMATION: Xaa can be any naturally occurring amino acid

```
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (305)..(305)
<223> OTHER INFORMATION: Xaa can be any naturally occurring amino acid

<400> SEQUENCE: 1

Met Cys Leu Glu Leu Val Leu Val Leu Ala Leu Asn Gly Val Leu
1               5                   10                  15

Ser Gln Ser Pro Gly Cys Asp Phe Ala Gln Asn Ile Ala Val Gly Thr
            20                  25                  30

Thr Val Asp Ile Ser Ser Pro Gly Tyr Pro Gly Asn Tyr Xaa Pro Gly
        35                  40                  45

Ile Gln Cys Arg Trp Ile Ala Thr Cys Xaa Val Gly Tyr Asn Cys Gln
50                  55                  60

Ile Asp Cys Pro Ile Ile Ser Ile Pro Gln Ser Ser Cys Ile Asp
65                  70                  75                  80

Arg Leu Leu Leu Ser Arg Thr Gly Asp Pro Gln Leu Ser Gly Ala Glu
                85                  90                  95

Val Tyr Cys Gly Arg Gly Thr Leu Ser Ala Thr Ser Val Gly Gln Arg
            100                 105                 110

Leu Ser Leu Gly Leu Ile Ser Ser Asn Ser Ser Pro Gly Gly Tyr Phe
        115                 120                 125

Arg Cys Arg Val Tyr Ala Val Ala Ser Ala Pro Ser Pro Ala Pro Cys
130                 135                 140

Arg Cys Gly Glu Arg Lys Gln Thr Arg Ile Val Gly Gly Glu Glu Ala
145                 150                 155                 160

Lys Ile Asn Glu Phe Arg Met Met Val Gly Leu Val Asp Ile Ser Ile
                165                 170                 175

Arg Gln Ile Lys Cys Gly Gly Ala Leu Ile Ser Asn Arg His Val Leu
            180                 185                 190

Thr Ala Ala His Cys Ile Ala Asn Gln Arg Thr Asp Asn Ile Gly Val
        195                 200                 205

Ile Val Gly Glu His Asp Val Ser Ser Gly Thr Glu Ser Ala Ala Gln
210                 215                 220

Gly Tyr Val Val Gln Arg Phe Ile Ile His Pro Leu Phe Thr Ala Ser
225                 230                 235                 240

Asn Tyr Asp Tyr Asp Val Ala Ile Val Glu Thr Thr Lys Glu Ile Thr
                245                 250                 255

Phe Ser Asp Ile Val Gly Pro Ala Cys Leu Pro Phe Lys Phe Val Asn
            260                 265                 270

Thr Asn Phe Thr Gly Leu Lys Val Thr Ile Leu Gly Trp Gly Thr Leu
        275                 280                 285

Phe Pro Gly Gly Pro Thr Ser Asn Val Leu Arg Lys Val Asp Leu Asp
290                 295                 300

Xaa Ile Ser Gln Ser Thr Cys Arg Ser Tyr Glu Ser Thr Leu Thr Asp
305                 310                 315                 320

Arg Gln Met Cys Thr Phe Thr Pro Gly Lys Asp Ala Cys Gln Asp Asp
                325                 330                 335

Ser Gly Gly Pro Leu Leu Tyr Thr Asp Pro Ser Thr Gly Leu Phe Phe
            340                 345                 350

Asn Leu Gly Ile Val Ser Tyr Gly Arg Phe Cys Ala Ser Asn Ser Pro
        355                 360                 365
```

Gly Ile Asn Met Arg Val Thr Ala Val Leu Asp Trp Ile Val Ser Ser
        370                 375                 380

Thr Gln Tyr Asn Phe Cys Arg Lys
385                 390

<210> SEQ ID NO 2
<211> LENGTH: 1179
<212> TYPE: DNA
<213> ORGANISM: Bombyx mori

<400> SEQUENCE: 2

| | | |
|---|---|---|
| atgtgccttg aacttgtatt ggttgtrctg gccttgaayg gcgtgttatc acagagcccg | 60 |
| ggatgcgact tygcgcaaaa tattgccgtc ggaactacgg tggatataag cagtccgggt | 120 |
| taccccggca actacmgtcc cggtattcaa tgtagatgga tagcgacatg tcycgttgga | 180 |
| tacaattgtc aaatagattg ccccataatm tccataccc aaagttcttc ttgcatagat | 240 |
| cgactattgc tctcraggac gggtgacccc caattgagtg gagccgaagt ctactgcggg | 300 |
| agaggaactt tatctgcaac ttctgttggc cagagactta gtttggggtt gatatcttca | 360 |
| aactcaagtc ccggtggata cttcaggtgt cgcgtatacg cggtggcatc agctcctagt | 420 |
| ccagcacctt gcagatgcgg ggaaaggaaa cagacccgca ttgtgggggg tgaagargck | 480 |
| aaaatcaatg aattccgaat gatggtcggg ttagttgata tcagcatcag gcaaatcaaa | 540 |
| tgcggaggcg ccttgatctc taatagrcat gtactgacyg cagcccattg tattgccaac | 600 |
| caaagaacgg ataacatagg agttatagtt ggagaacacg atgtttccag cggcacagaa | 660 |
| tcggcagctc agggttacgt agtacaaagg tttattatac atccattatt tactgcttcc | 720 |
| aattatgact acgacgtggc satagtggaa acaacaaagg aaataacatt cagcgatata | 780 |
| gttggaccgg cttgtctacc gttcaagttc gtcaatacca atttcactgg cttaaaagtt | 840 |
| accattcttg gttggggaac gttattcccg ggaggtccaa cgtctaatgt tctccgtaag | 900 |
| gtagacctgg acgtcatcag ccagagcacc tgtaggagtt acgagtcgac actgacggac | 960 |
| agacagatgt gcacattcac tcctgggaag gacgcgtgtc aagacgactc cggtggccct | 1020 |
| ctgctctata cagacccgag taccggattg ttcttcaacc tgggcatcgt gagttacggt | 1080 |
| cgtttctgcg catcaaacag tccgggcatc aacatgagag tcaccgcagt actggactgg | 1140 |
| atcgtctcgt ccacgcaata taacttctgc aggaaataa | 1179 |

<210> SEQ ID NO 3
<211> LENGTH: 1179
<212> TYPE: DNA
<213> ORGANISM: Bombyx mori
<220> FEATURE:
<221> NAME/KEY: CDS
<222> LOCATION: (1)..(1179)

<400> SEQUENCE: 3 atg tgc ctt gaa ctt gta ttg gtt gta ctg gcc ttg aat ggc gtg tta      48
Met Cys Leu Glu Leu Val Leu Val Val Leu Ala Leu Asn Gly Val Leu
 1               5                  10                  15 tca cag agc ccg gga tgc gac ttt gcg caa aat att gcc gtc gga act      96
Ser Gln Ser Pro Gly Cys Asp Phe Ala Gln Asn Ile Ala Val Gly Thr
             20                  25                  30 acg gtg gat ata agc agt ccg ggt tac ccc ggc aac tac cgt ccc ggt     144
Thr Val Asp Ile Ser Ser Pro Gly Tyr Pro Gly Asn Tyr Arg Pro Gly
         35                  40                  45

-continued

| | |
|---|---|
| att caa tgt aga tgg ata gcg aca tgt ccc gtt gga tac aat tgt caa<br>Ile Gln Cys Arg Trp Ile Ala Thr Cys Pro Val Gly Tyr Asn Cys Gln<br>50                                55                              60 | 192 |
| ata gat tgc ccc ata atc tcc ata ccc caa agt tct tct tgc ata gat<br>Ile Asp Cys Pro Ile Ile Ser Ile Pro Gln Ser Ser Ser Cys Ile Asp<br>65                               70                         75                             80 | 240 |
| cga cta ttg ctc tca agg acg ggt gac ccc caa ttg agt gga gcc gaa<br>Arg Leu Leu Leu Ser Arg Thr Gly Asp Pro Gln Leu Ser Gly Ala Glu<br>                              85                         90                         95 | 288 |
| gtc tac tgc ggg aga gga act tta tct gca act tct gtt ggc cag aga<br>Val Tyr Cys Gly Arg Gly Thr Leu Ser Ala Thr Ser Val Gly Gln Arg<br>                100                      105                      110 | 336 |
| ctt agt ttg ggg ttg ata tct tca aac tca agt ccc ggt gga tac ttc<br>Leu Ser Leu Gly Leu Ile Ser Ser Asn Ser Ser Pro Gly Gly Tyr Phe<br>         115                      120                      125 | 384 |
| agg tgt cgc gta tac gcg gtg gca tca gct cct agt cca gca cct tgc<br>Arg Cys Arg Val Tyr Ala Val Ala Ser Ala Pro Ser Pro Ala Pro Cys<br>130                             135                      140 | 432 |
| aga tgc ggg gaa agg aaa cag acc cgc att gtg ggg ggt gaa gag gcg<br>Arg Cys Gly Glu Arg Lys Gln Thr Arg Ile Val Gly Gly Glu Glu Ala<br>145                           150                      155                      160 | 480 |
| aaa atc aat gaa ttc cga atg atg gtc ggg tta gtt gat atc agc atc<br>Lys Ile Asn Glu Phe Arg Met Met Val Gly Leu Val Asp Ile Ser Ile<br>                        165                      170                      175 | 528 |
| agg caa atc aaa tgc gga ggc gcc ttg atc tct aat aga cat gta ctg<br>Arg Gln Ile Lys Cys Gly Gly Ala Leu Ile Ser Asn Arg His Val Leu<br>         180                      185                      190 | 576 |
| acc gca gcc cat tgt att gcc aac caa aga acg gat aac ata gga gtt<br>Thr Ala Ala His Cys Ile Ala Asn Gln Arg Thr Asp Asn Ile Gly Val<br>                195                      200                      205 | 624 |
| ata gtt gga gaa cac gat gtt tcc agc ggc aca gaa tcg gca gct cag<br>Ile Val Gly Glu His Asp Val Ser Ser Gly Thr Glu Ser Ala Ala Gln<br>         210                      215                      220 | 672 |
| ggt tac gta gta caa agg ttt att ata cat cca tta ttt act gct tcc<br>Gly Tyr Val Val Gln Arg Phe Ile Ile His Pro Leu Phe Thr Ala Ser<br>225                           230                      235                      240 | 720 |
| aat tat gac tac gac gtg gcg ata gtg gaa aca aca aag gaa ata aca<br>Asn Tyr Asp Tyr Asp Val Ala Ile Val Glu Thr Thr Lys Glu Ile Thr<br>                        245                      250                      255 | 768 |
| ttc agc gat ata gtt gga ccg gct tgt cta ccg ttc aag ttc gtc aat<br>Phe Ser Asp Ile Val Gly Pro Ala Cys Leu Pro Phe Lys Phe Val Asn<br>         260                      265                      270 | 816 |
| acc aat ttc act ggc tta aaa gtt acc att ctt ggt tgg gga acg tta<br>Thr Asn Phe Thr Gly Leu Lys Val Thr Ile Leu Gly Trp Gly Thr Leu<br>                275                      280                      285 | 864 |
| ttc ccg gga ggt cca acg tct aat gtt ctc cgt aag gta gac ctg gac<br>Phe Pro Gly Gly Pro Thr Ser Asn Val Leu Arg Lys Val Asp Leu Asp<br>290                           295                      300 | 912 |
| gtc atc agc cag agc acc tgt agg agt tac gag tcg aca ctg acg gac<br>Val Ile Ser Gln Ser Thr Cys Arg Ser Tyr Glu Ser Thr Leu Thr Asp<br>305                           310                      315                      320 | 960 |
| aga cag atg tgc aca ttc act cct ggg aag gac gcg tgt caa gac gac<br>Arg Gln Met Cys Thr Phe Thr Pro Gly Lys Asp Ala Cys Gln Asp Asp<br>                325                      330                      335 | 1008 |
| tcc ggt ggc cct ctg ctc tat aca gac ccg agt acc gga ttg ttc ttc<br>Ser Gly Gly Pro Leu Leu Tyr Thr Asp Pro Ser Thr Gly Leu Phe Phe<br>         340                      345                      350 | 1056 |
| aac ctg ggc atc gtg agt tac ggt cgt ttc tgc gca tca aac agt ccg<br>Asn Leu Gly Ile Val Ser Tyr Gly Arg Phe Cys Ala Ser Asn Ser Pro<br>         355                      360                      365 | 1104 |

```
ggc atc aac atg aga gtc acc gca gta ctg gac tgg atc gtc tcg tcc    1152
Gly Ile Asn Met Arg Val Thr Ala Val Leu Asp Trp Ile Val Ser Ser
370             375                 380 acg caa tat aac ttc tgc agg aaa taa                                1179
Thr Gln Tyr Asn Phe Cys Arg Lys
385                 390
```

<210> SEQ ID NO 4
<211> LENGTH: 392
<212> TYPE: PRT
<213> ORGANISM: Bombyx mori

<400> SEQUENCE: 4

```
Met Cys Leu Glu Leu Val Leu Val Leu Ala Leu Asn Gly Val Leu
1               5                   10                  15

Ser Gln Ser Pro Gly Cys Asp Phe Ala Gln Asn Ile Ala Val Gly Thr
            20                  25                  30

Thr Val Asp Ile Ser Ser Pro Gly Tyr Pro Gly Asn Tyr Arg Pro Gly
        35                  40                  45

Ile Gln Cys Arg Trp Ile Ala Thr Cys Pro Val Gly Tyr Asn Cys Gln
50                  55                  60

Ile Asp Cys Pro Ile Ile Ser Ile Pro Gln Ser Ser Cys Ile Asp
65                  70                  75                  80

Arg Leu Leu Leu Ser Arg Thr Gly Asp Pro Gln Leu Ser Gly Ala Glu
                85                  90                  95

Val Tyr Cys Gly Arg Gly Thr Leu Ser Ala Thr Ser Val Gly Gln Arg
            100                 105                 110

Leu Ser Leu Gly Leu Ile Ser Ser Asn Ser Ser Pro Gly Gly Tyr Phe
        115                 120                 125

Arg Cys Arg Val Tyr Ala Val Ala Ser Ala Pro Ser Pro Ala Pro Cys
130                 135                 140

Arg Cys Gly Glu Arg Lys Gln Thr Arg Ile Val Gly Gly Glu Glu Ala
145                 150                 155                 160

Lys Ile Asn Glu Phe Arg Met Met Val Gly Leu Val Asp Ile Ser Ile
                165                 170                 175

Arg Gln Ile Lys Cys Gly Gly Ala Leu Ile Ser Asn Arg His Val Leu
            180                 185                 190

Thr Ala Ala His Cys Ile Ala Asn Gln Arg Thr Asp Asn Ile Gly Val
        195                 200                 205

Ile Val Gly Glu His Asp Val Ser Ser Gly Thr Glu Ser Ala Ala Gln
210                 215                 220

Gly Tyr Val Val Gln Arg Phe Ile Ile His Pro Leu Phe Thr Ala Ser
225                 230                 235                 240

Asn Tyr Asp Tyr Asp Val Ala Ile Val Glu Thr Thr Lys Glu Ile Thr
                245                 250                 255

Phe Ser Asp Ile Val Gly Pro Ala Cys Leu Pro Phe Lys Phe Val Asn
            260                 265                 270

Thr Asn Phe Thr Gly Leu Lys Val Thr Ile Leu Gly Trp Gly Thr Leu
        275                 280                 285

Phe Pro Gly Gly Pro Thr Ser Asn Val Leu Arg Lys Val Asp Leu Asp
290                 295                 300

Val Ile Ser Gln Ser Thr Cys Arg Ser Tyr Glu Ser Thr Leu Thr Asp
305                 310                 315                 320

Arg Gln Met Cys Thr Phe Thr Pro Gly Lys Asp Ala Cys Gln Asp Asp
                325                 330                 335
```

Ser Gly Gly Pro Leu Leu Tyr Thr Asp Pro Ser Thr Gly Leu Phe Phe
            340                 345                 350

Asn Leu Gly Ile Val Ser Tyr Gly Arg Phe Cys Ala Ser Asn Ser Pro
        355                 360                 365

Gly Ile Asn Met Arg Val Thr Ala Val Leu Asp Trp Ile Val Ser Ser
    370                 375                 380

Thr Gln Tyr Asn Phe Cys Arg Lys
385                 390

<210> SEQ ID NO 5
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 5
gtnbtnwcng cngcncaytg                                              20

<210> SEQ ID NO 6
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

```
<400> SEQUENCE: 6
avnggnccnc cngartcncc                                              20

<210> SEQ ID NO 7
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 7
ccngartcnc cntkrcang                                               19

<210> SEQ ID NO 8
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 8
taatacgact cactataggg cga                                          23

<210> SEQ ID NO 9
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 9
atttaggtga cactatagaa tac                                          23

<210> SEQ ID NO 10
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 10
ccacgtcgta gtcataattg                                              20
```

```
<210> SEQ ID NO 11
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 11
taaccctgag ctgccgatgc tgt                                              23

<210> SEQ ID NO 12
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 12
gctggaaaca tcgtgttctc caa                                              23

<210> SEQ ID NO 13
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 13
ggccacgcgt cgactagtac                                                  20

<210> SEQ ID NO 14
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 14
ggccacgcgt cgactagtac gggnngggnn gggnng                                36

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
ttcttggttg gggaacgtta ttc                                              23
```

```
<210> SEQ ID NO 16
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 16
acgtctaatg ttctccgtaa ggt                                              23

<210> SEQ ID NO 17
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 17
ggccacgcgt cgactagtac                                                  20

<210> SEQ ID NO 18
<211> LENGTH: 37
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 18
ggccacgcgt cgactagtac tttttttttt ttttttt                               37

<210> SEQ ID NO 19
<211> LENGTH: 34
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 19
tctcggtccg tcagaaatgt gccttgaact tgta                                  34

<210> SEQ ID NO 20
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<223> OTHER INFORMATION: Primer

<400> SEQUENCE: 20
ccaagcttat ttcctgcaga agttatattg cg                                    32
```